United States Patent
Lawandy

[11] Patent Number: 5,845,640
[45] Date of Patent: Dec. 8, 1998

[54] CHEMILUMINESCENT SOURCES FOR PHOTODYNAMIC THERAPY AND PHOTOMEDICINE

[75] Inventor: Nabil M. Lawandy, North Kingston, R.I.

[73] Assignee: Spectra Science Corporation, Providence, R.I.

[21] Appl. No.: 929,782

[22] Filed: Sep. 15, 1997

Related U.S. Application Data

[60] Provisional application No. 60/036,246 Jan. 24, 1997.

[51] Int. Cl.$^6$ ........................................................... A61B 6/00
[52] U.S. Cl. .......................... 128/664; 128/665; 128/654; 604/20
[58] Field of Search ..................................... 128/654, 664, 128/665, 666, 663; 607/88, 89, 7; 606/2, 3, 9, 27; 604/20, 49

[56] References Cited

U.S. PATENT DOCUMENTS

| | | | |
|---|---|---|---|
| 4,889,129 | 12/1989 | Dougherty et al. | 128/664 |
| 4,917,084 | 4/1990 | Sinofsky | 606/7 |
| 4,930,504 | 6/1990 | Diamantopoulos et al. | 128/395 |
| 4,957,481 | 9/1990 | Gatenby | 604/20 |
| 5,092,841 | 3/1992 | Spears | 604/96 |
| 5,111,821 | 5/1992 | Potter | 128/654 |
| 5,527,350 | 6/1996 | Grove et al. | 607/89 |
| 5,572,996 | 11/1996 | Doriron et al. | 128/633 |
| 5,625,456 | 4/1997 | Lawandy | 356/376 |

OTHER PUBLICATIONS

"Selective Absorption of Ultraviolet Laser Energy by Human Atherosclerotic Plaque Treated with Tetracycline", Douglas Murphy–Chutorian et al., American Journal of Cardiology, vol. 55, May 1, 1985, pp. 1293–1297.

*Primary Examiner*—John G. Weiss
*Assistant Examiner*—David J. Cho
*Attorney, Agent, or Firm*—Perman & Green, LLP

[57] ABSTRACT

An optical source (10) for exciting a photosensitive drug that responds to light within a predetermined band of wavelengths. The optical source uses a chemiluminescent source in combination with at least one fluorescer selected to output light within the predetermined band of wavelengths. The chemiluminescent source can be flowed during use. In one embodiment the chemiluminescent source is stored in a heated reservoir, and is pumped from the reservoir through a conduit, such as a catheter. A patch can be used for spreading the chemiluminescent source over a wider area. An active feedback system can also be used for controlling the output light. In preferred embodiments a plurality of reactants are mixed for forming a chemiluminescent source in combination with at least one fluorescer selected to output light within the predetermined band of wavelengths. The mixing of the reactants causes an excitation of the at least one selected fluorescer by energy transfer from an energetic immediate in a chemiluminescent reaction to provide a fluorescent emission in the predetermined band of wavelengths.

26 Claims, 2 Drawing Sheets

CHEMILUMINESCENT SOURCES FOR PHOTODYNAMIC THERAPY AND PHOTOMEDICINE

This application claims the benefit of U.S. provisional application(s) No(s). 60/036,246, Jan. 24, 1997.

FIELD OF THE INVENTION

This invention relates generally to optically-based therapeutic procedures.

BACKGROUND OF THE INVENTION

Photodynamic Therapy (PDT) uses specifically designed drugs such as FOSCAN (Scotia Pharmaceuticals), a photodynamic therapy related drug, ALA (DUSA) and Photofrin (QLT Phototherapeutics) to destroy rapidly dividing cells. These drugs are selectively retained or generated at rapidly dividing cells and are subsequently excited by light to produce the desired effects. The primary mode of activity usually involves energy transfer from these photoexcited drugs to $O_2$ to produce superoxides or $O_2$ in the singlet state. To date this excitation has been provided by lasers, lamps, and new materials such as LASERPRINT (a new material which provides laser action in amplifying scattering media). Some of these sources are expensive and require complicated delivery systems.

OBJECTS OF THE INVENTION

It is an object of this invention to provide an improved method and apparatus to excite an optically-responsive or photosensitive therapeutic drug.

It is a further object of this invention to provide an improved method and apparatus for generating light that can be used directly for photomedicine applications.

SUMMARY OF THE INVENTION

The foregoing and other problems are overcome and the object of the invention is realized by methods and apparatus in accordance with embodiments of this invention.

This invention teaches the use of static or flowing chemiluminescent materials to excite a photosensitive drug or to irradiate a tissue for performing photomedicine. Many reactions can be used for chemiluminescence, and include luciferase (Firefly reaction) and the oxalate ester/hydrogen peroxide ($H_2O_2$) system. The latter reaction is commonly found in so-called "light sticks".

The fluorescers in the chemiluminescent reaction can be selected so as to emit exactly under the absorption band of many photosensitive drugs, such as those used in PDT, or those found in living systems, such as blood.

For example, rhodamine derivatives can be used for exciting the photoresponsive drugs Photofrin, ALA, PP IX, and FOSCAN, a photodynamic therapy related drug.

In order to sustain high luminous fluxes, the reaction can be created in a reservoir with a constant input of reactants and pumped through a catheter or a fluid containing externally applied patch, depending on the procedure. Catheters are ideally suited for treating, by example, esophageal cancer, while patches are ideally suited for treating skin conditions, as well as head and neck cancers. The reactants can be heated to increase the reaction rates and produce higher optical power.

The use of patches for skin and oral cavity treatments can eliminate the need for anesthesia, and furthermore can allow the patient to continue the treatment outside of the clinical setting. Patches may be made to operate in a similar manner to light sticks, and can be initiated by a pressure rupture of a barrier, releasing the reactants into a transparent pouch. One side of the pouch may be reflective so as to enhance the delivery of light towards the target area.

Active feedback can be provided from the target area using, by example, a photodiode, so as to control the delivery of reactants to, and the output power of the reactants at, the target area.

In preferred embodiments of this invention a plurality of reactants are mixed for forming a chemiluminescent source in combination with at least one fluorescer selected to output light within the predetermined band of wavelengths. The mixing of the reactants causes an excitation of the at least one selected fluorescer by energy transfer from an energetic key immediate in the chemiluminescent reaction to provide a fluorescent emission in the predetermined band of wavelengths.

BRIEF DESCRIPTION OF THE DRAWINGS

The above set forth and other features of the invention are made more apparent in the ensuing Detailed Description of the Invention when read in conjunction with the attached Drawings, wherein.

DETAILED DESCRIPTION OF THE INVENTION

Figure 1:
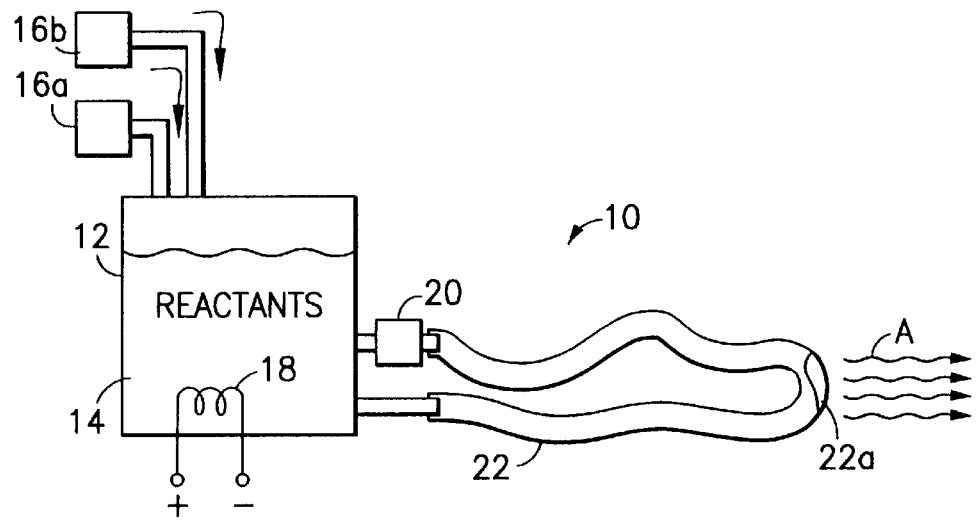
FIG. 1 is block diagram of a system for delivering a flowing chemiluminescent source to a region of interest.

Referring to FIG. 1, there is illustrated a system 10 for flowing a chemiluminescent source. System 10 includes a reservoir 12 for containing a volume of reactants 14. Coupled to the reservoir 12 are a plurality of reactant sources 16a, 16b which provide, either continuously or on demand, measured amounts of reactants to the reservoir 12 so as to provide a desired intensity of emitted light. A heater 18 can be provided for heating the reactants 14 so as to increase the reaction rate, to produce a higher optical output, as well as to control the optical power. The reactants include at least one selected fluorescer, such as a rhodamine derivative, that is selected for its emission of a wavelength that optically excites a photosensitive drug of interest. The reactants also include materials known for use in providing chemiluminescence, such as luciferase and the oxalate ester/hydrogen peroxide ($H_2O_2$) system.

Suitable fluorescers for use with this invention include the following:

Coumarin 440

Coumarin 480

9,10-diphenylanthacene (DPA)

Rhodamine 590
Rhodamine 610
Rhodamine 640
Rhodamine tetrafluoroborate
Sulforhodamine 640
DCM
Kiton red 620
Acridine orange The enhancement capacity of $TiO_2$ for different dyes (Ester, dye+Peroxide with and without $TiO_2$ was confirmed for the following:

Rubrene (yellow emission)
9,10-bis(phenylethynyl)anthracene (yellow)
Coumarin 480 (blue)
9,10-diphenylanthacene (DPA)

In the foregoing examples, the number following the compound name indicates the emission wavelength.

The teaching of this invention is believed to produce satisfactory results using peroxyoxalate chemiluminescent systems (PO CL). In these systems, oxalic acid derivatives react with hydrogen peroxide in the presence of a fluorophore to produce a bright emission characteristic of the fluorescer. This reaction proceeds via an energetic key intermediate, which is proposed to be 1, 2-dioxetanedione.

Other oxalate esters include the following.

Bis(2-nitrophenyl)
Bis(4-nitrophenyl)
Bis(4-nitro 3-trifluoromethyl)
Bis(4-nitro-2-formylphenyl)
Bis(4-nitro-2,6-dichlorophenyl)
Bis(2.4-dinitrophenyl)
Bis(2,5-dinitrophenyl)
Bis(2,4-dichlorophenyl)
Bis(pentacholorophenyl)
Bis(pentafluorophenyl)
Bis(3-trifluoro-methylphenyl)
Bis(3.5-di(trifluoro-methylphenyl)
Bis(2,6-dimethylphenyl)
Bis(4-methoxyphenyl)
Diphenyl
Phenylene
Bis(2-naphthyl)
Di-i-butyl
Bis(2-cyano-2-propyl)
Bis(2,2,2-trifluoro-ethyl
Bis(diphenylmethyl)

Another oxalate ester of interest is bis(2,4,6-trichlorophenyl) oxalate.

In an exemplary embodiment of this invention a Rhodamine derivative is excited by energy transfer from an energetic immediate in the chemiluminescent reaction, and provides a fluorescent emission in a desired band of wavelengths. A second emitter (e.g., a dye, chelate, or phosphor) can be used to coat a portion of structure, such as the catheter described below, to further shift the emission to a desired wavelength. A pump 20 is provided for pumping a flow of the reactants 14 through a conduit, such as a catheter 22, for delivering the chemiluminescent source to a region of tissue to be treated, as well as to control the output optical power. At least one portion of the catheter 22 is transparent to the light emission having the wavelengths used to excite a photosensitive drug of interest. FIG. 1 illustrates the use of a single transparent region 22a for outputting light A having the desired wavelengths.

It can be appreciated that the reactants can be pumped into a waste tank (not shown), and need not be returned to the reservoir 12.

Figure 2:
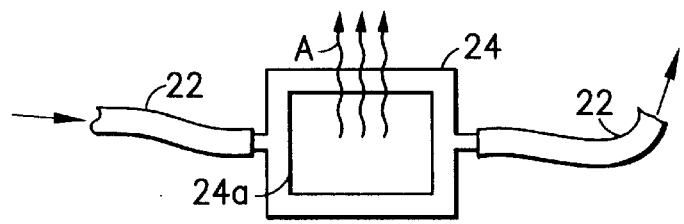
FIG. 2 illustrates a first embodiment of a patch suitable for being connected to the system of FIG. 1.

FIG. 2 shows an embodiment wherein a patch 24 is inserted into the catheter 22 such that the flow of reactants passes through the patch 24. The patch has at least one internal chamber or compartment capable of containing the flow of reactants as they pass through. The use of the patch 24 beneficially spreads the flowing chemiluminescent source over a wider area, which is useful for treating certain tissues such as skin. As in the catheter embodiment of FIG. 1, the patch 24 has at least one region 24a that is transparent to the light A having the wavelengths of interest.

Figure 3A:
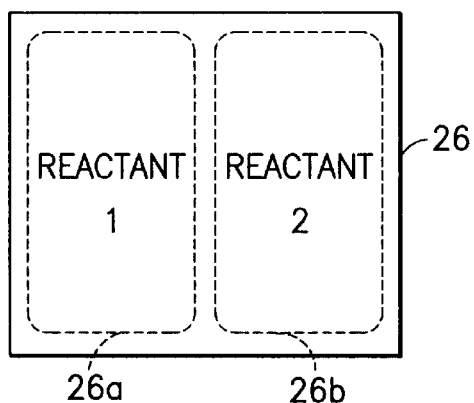
FIG. 3A illustrates a top view of a second embodiment of a patch, wherein reactants can be mixed on demand for generating the chemiluminescent source.
Figure 3B:
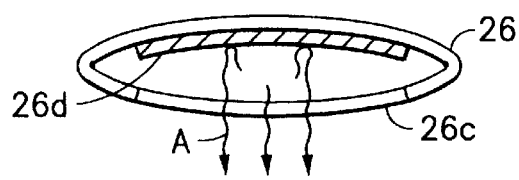
FIG. 3B illustrates the cross-sectional side view of the second embodiment of the patch in FIG. 3A, wherein reactants can be mixed on demand for generating the chemiluminescent source.

FIG. 3A illustrates a top view and FIG. 3B a cross-sectional side view of an embodiment wherein a partially transparent patch 26 includes a plurality of reactant compartments or containers 26a, 26b which, when broken or ruptured by a mechanical deformation of the patch, enable the reactants to be mixed and thus provide the desired therapeutic light. Although two reactants are shown in FIGS. 1 and 3A, it can be realized that as many reactants as are needed can be utilized in accordance with this invention. At least one of the reactants also contains the one or more selected fluorescers, or the fluorescer(s) could be provided in a separate compartment or container.

As is seen in FIG. 3B the patch 26 includes a transparent window portion 26c, and may include a reflector 26d, such as a layer of foil, disposed on an opposite surface for reflecting incident light towards the window portion 26c. The reflector 26d can be used as well in the embodiments of FIGS. 1 and 2. A portion of the reflector 26d, or some other structure in the patch 26, could include the above-mentioned second emitter (e.g., a dye, chelate, or phosphor) in order to shift the emission to a desired wavelength.

Figure 4:
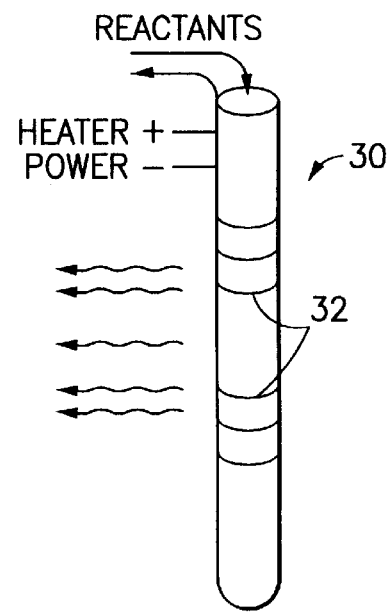
FIG. 4 illustrates an embodiment of a catheter that is useful for esophageal and other applications.

FIG. 4 illustrates an embodiment of a transparent or partially transparent catheter 30 that is useful for esophageal and other applications. A flow of reactants is established through the catheter 30 for providing the desired light emission A. A set of heating coils or tape 32, such as a resistive heating strip, can be used to produce a desired non-uniform excitation profile to treat different regions with dose selectivity. The coils 32 are preferably of low wattage, and may be molded into or embedded within the catheter wall. The reflector 26d can also be used if desired.

Figure 5:
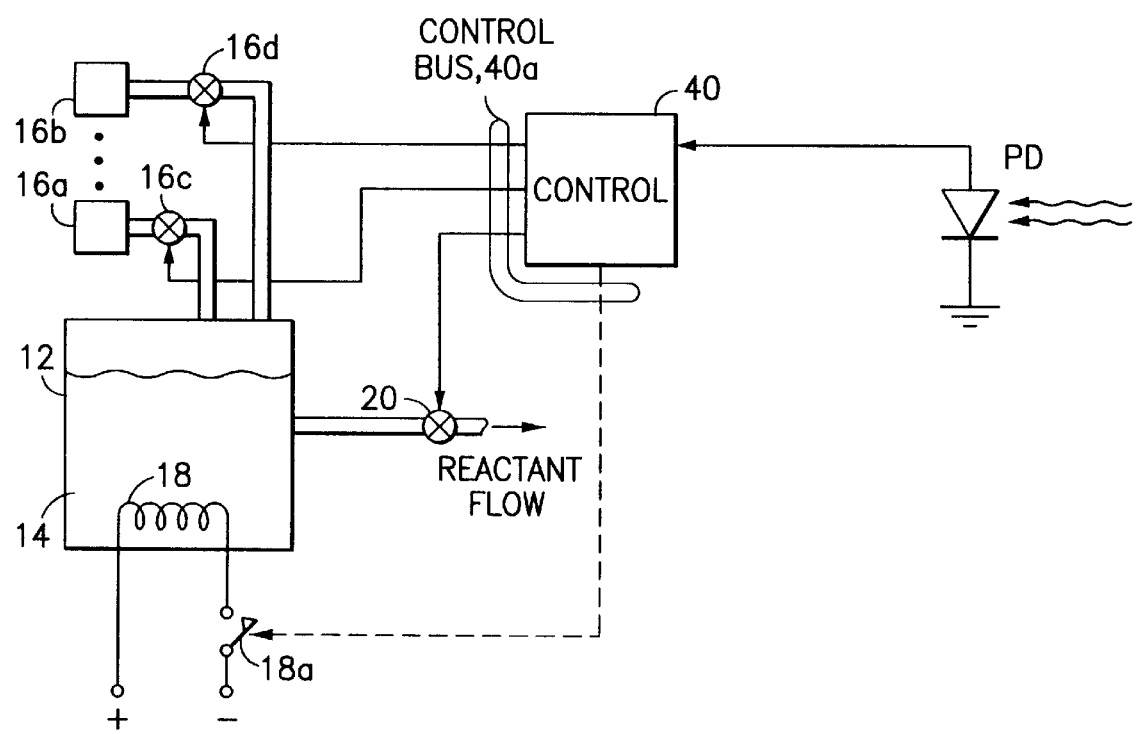
FIG. 5 is a block diagram of the system shown in FIG. 1, wherein active feedback is used.

FIG. 5 shows the embodiment of FIG. 1 wherein a photodiode (PD) is used to provide an in-situ measure of output light dosage. The output of the photodiode is coupled to a controller 40 having an associated control bus 40a. The control bus 40a, in this example, is coupled to the pump 20, to reactant source pumps 16c and 16d, and to a heater controller 18a (shown schematically as a switch). Based on the light intensity detected by the photodiode in the target area, the controller is enabled to selectively control one or more reactant parameters (e.g., temperature, concentration, flow rate, etc.) so as to provide a desired amount of light energy to the target area. Other optical detectors, such as photoresistors, can be used in place of the photodiode.

While the invention has been particularly shown and described with respect to preferred embodiments thereof, it will be understood by those skilled in the art that changes in form and details may be made therein without departing from the scope and spirit of the invention.

What is claimed is:

1. An optical source for exciting a photosensitive drug that responds to light within a predetermined band of wavelengths, comprising a chemiluminescent source in combination with at least one fluorescer selected to output light within the predetermined band of wavelengths;

wherein said chemiluminescent source, in combination with said at least one fluorescer, is provided as a plurality of reactants, and further comprising:
a reservoir wherein said reactants are mixed; and
a pump for pumping the mixed reactants through a conduit to a tissue to be treated.

2. The optical source as in claim 1, wherein the chemiluminescent source is flowed during use.

3. The optical source as in claim 1, and further comprising means for heating said chemiluminescent source.

4. The optical source as in claim 1, and further comprising an active feedback system for controlling said output light.

5. The optical source as in claim 1, wherein said chemiluminescent source in combination with said at least one fluorescer are flowed through a conduit.

6. The optical source as in claim 1, wherein said chemiluminescent source is comprised of an oxalate ester/hydrogen peroxide ($H_2O_2$) system.

7. The optical source as in claim 1, wherein said chemiluminescent source is comprised of luciferase.

8. The optical source as in claim 1, wherein said at least one selected fluorescer is comprised of a rhodamine derivative.

9. The optical source as in claim 1, and further comprising a second fluorescer selected for shifting emission wavelengths of said at least one fluorescer.

10. An optical source for exciting a photosensitive drug that responds to light within a predetermined band of wavelengths, comprising a chemiluminescent source in combination with at least one fluorescer selected to output light within the predetermined band of wavelengths;

wherein said chemiluminescent source, in combination with said at least one fluorescer, is provided as a plurality of reactants, and further comprising:
a patch comprising a plurality of compartments, individual ones of said compartments containing one of said reactants; wherein
a mechanical deformation of said patch causes said compartments to rupture such that said reactants are released and mixed together.

11. The optical source as in claim 10, wherein said chemiluminescent source is comprised of at least one of an oxalate ester/hydrogen peroxide ($H_2O_2$) system or of luciferase.

12. The optical source as in claim 10, and further comprising a second fluorescer selected for shifting emission wavelengths of said at least one fluorescer.

13. A catheter for insertion into a body cavity, said catheter having at least one region that is transparent to light having wavelengths within a predetermined band of wavelengths selected for exciting a photosensitive drug, said catheter comprising a conduit for flowing a chemiluminescent source in combination with at least one fluorescer selected to output light within the predetermined band of wavelengths.

14. A patch for application to a surface of a tissue, said patch having at least one region that is transparent to light having wavelengths within a predetermined band of wavelengths selected for exciting a photosensitive drug, said patch comprising an internal chamber region for flowing therethrough a chemiluminescent source in combination with at least one fluorescer selected to output light within the predetermined band of wavelengths.

15. A patch for application to a surface of a tissue, said patch having at least one region that is transparent to light having wavelengths within a predetermined band of wavelengths selected for exciting a photosensitive drug, said patch having at least one region that is transparent to light having wavelengths within a predetermined band of wavelengths selected for exciting a photosensitive drug, said patch comprising a plurality of compartments, individual ones of said compartments containing one of a plurality of reactants; wherein a mechanical deformation of said patch causes said compartments to rupture such that said reactants are released and mixed together for forming a chemiluminescent source in combination with at least one fluorescer selected to output light within the predetermined band of wavelengths.

16. A method for generating light having wavelengths within a predetermined band of wavelengths selected for exciting a photosensitive drug, comprising steps of:

mixing a plurality of reactants for forming a chemiluminescent source in combination with at least one fluorescer selected to output light within the predetermined band of wavelengths;

exciting the at least one selected fluorescer by energy transfer from an energetic immediate in a chemiluminescent reaction to provide a fluorescent emission in the predetermined band of wavelengths; and optically coupling the fluorescent emission to a tissue to be treated by the photosensitive drug.

17. The method as in claim 16, wherein the step of mixing includes a step of mixing the reactants in a reservoir, and wherein the step of optically coupling includes a step of causing a flow of the chemiluminescent source in combination with the at least one fluorescer to the tissue to be treated.

18. The method as in claim 16, wherein the step of mixing includes a step of combining the reactants within a patch that is to be applied to a surface of a tissue to be treated.

19. The method as in claim 18, wherein the step of combining includes an initial step of rupturing a plurality of reactant containing compartments within the patch.

20. A source of light having wavelengths within a predetermined band of wavelengths selected for exciting a photosensitive drug, comprising:

means for mixing a plurality of reactants for forming a chemiluminescent source in combination with at least one fluorescer selected to output light within the predetermined band of wavelengths, said mixing means causing an excitation of the at least one selected fluorescer by energy transfer from an energetic immediate in a chemiluminescent reaction to provide a fluorescent emission in the predetermined band of wavelengths; and means for optically coupling the fluorescent emission to a tissue to be treated by the photosensitive drug.

21. The source as in claim 20, wherein said mixing means is comprised of:
a reservoir coupled to a plurality of reactant sources;
means for introducing reactants from said plurality of reactant sources into said reservoir; and
means for causing a flow of mixed reactants out of said reservoir.

22. The source as in claim 20, wherein said means for optically coupling is comprised of a catheter having a transparent region.

23. The source as in claim 20, wherein said means for optically coupling is comprised of a patch having a transparent region.

24. The source as in claim 23, wherein said mixing occurs within said patch.

25. The source as in claim 20, and further comprising means for maintaining said chemiluminescent source at a predetermined temperature.

26. The source as in claim 20, and further comprising an active feedback system for controlling an intensity of said fluorescent emission.

* * * * *